(12) United States Patent
Gerking et al.

(10) Patent No.: US 6,875,839 B2
(45) Date of Patent: Apr. 5, 2005

(54) METHOD FOR PRODUCING POLYLACTIC ACID AND CORRESPONDING DEVICE

(75) Inventors: Lüder Gerking, Berlin (DE); Rainer Hagen, Berlin (DE); Klaus Richter, Leipzig (DE); Frank Idler, Potsdam (DE); Winfried Reimann, Potsdam (DE); Bernd Hanzsch, Geltow (DE)

(73) Assignee: Inventa-Fischer GmbH & Co. KG, Berlin (DE)

( * ) Notice: Subject to any disclaimer, the term of this patent is extended or adjusted under 35 U.S.C. 154(b) by 48 days.

(21) Appl. No.: 10/258,036

(22) PCT Filed: Apr. 19, 2001

(86) PCT No.: PCT/EP01/04482

§ 371 (c)(1),
(2), (4) Date: Jan. 30, 2003

(87) PCT Pub. No.: WO01/81610

PCT Pub. Date: Nov. 1, 2001

(65) Prior Publication Data

US 2003/0158360 A1 Aug. 21, 2003

(30) Foreign Application Priority Data

Apr. 20, 2000 (DE) .......................................... 100 20 898

(51) Int. Cl.[7] .............................. C08G 53/08; C12P 7/56
(52) U.S. Cl. ....................... 528/354; 528/357; 549/274; 435/139; 435/289.1; 422/131
(58) Field of Search ................................. 528/354, 357; 549/274; 435/139, 289.1; 422/131

(56) References Cited

U.S. PATENT DOCUMENTS

| | | |
|---|---|---|
| 5,357,035 A | 10/1994 | Gruber et al. |
| 5,503,750 A | 4/1996 | Russo, Jr. et al. |
| 5,521,278 A | 5/1996 | O'Brien et al. |
| 5,801,255 A | 9/1998 | Ohara et al. |
| 6,005,067 A | 12/1999 | Gruber et al. |
| 6,596,521 B1 * | 7/2003 | Chang et al. ................ 435/136 |

FOREIGN PATENT DOCUMENTS

| | | |
|---|---|---|
| AT | 144346 | 8/1933 |
| DE | 19631633 A | 8/1996 |
| DE | 19718608 A | 5/1997 |
| EP | 0777664 B | 5/1996 |
| FR | 2599751 A | 6/1986 |
| PL | 63329 | 3/1967 |
| WO | WO 95/09879 A | 4/1995 |

OTHER PUBLICATIONS

Ackermann, "Processses for production and use of renewable raw materials," *ATB—Jahresbericht 1999*, 48–59 (2000).

Hofvendahl et al., "Simultaneous enzymatic wheat starch saccharification and fermentation to lactic acid by *Lactcoccus lactis*," *Appl. Microbi9ol Biotechnol*, 52, 163–169 (1999).

Javanainen et al., "Lactic Acid Fermentation on Barley Flour Without Additional Nutrients," *Biotechnology Techniques*, Vo. 9, No. 8, 543–548 (1995).

Payot et al., Lactic acid production by *Bacillus coagulans*—Kinetic studies and optimization of culture medium for batch and continuous fermentations, *enzyme and Microbial Technology*, 24, 191–199 (1999).

* cited by examiner

*Primary Examiner*—Fred M Teskin
(74) *Attorney, Agent, or Firm*—Leydig, Voit & Mayer, Ltd.

(57) ABSTRACT

The invention relates to a method for producing polylactic acid, comprising the steps of obtaining lactic acid from starchy agricultural products by fermentation, ultrapurification of the lactic acid by ultrafiltration, nanofiltration and/or electrodialysis, concentration of the lactic acid and production of a prepolymer, cyclizing depolymerization to dilactide, purification of the dilactide, ring-opening polymerization of the dilactide and demonomerization of the polylactide.

35 Claims, 8 Drawing Sheets

METHOD FOR PRODUCING POLYLACTIC ACID AND CORRESPONDING DEVICE

Figure 1:
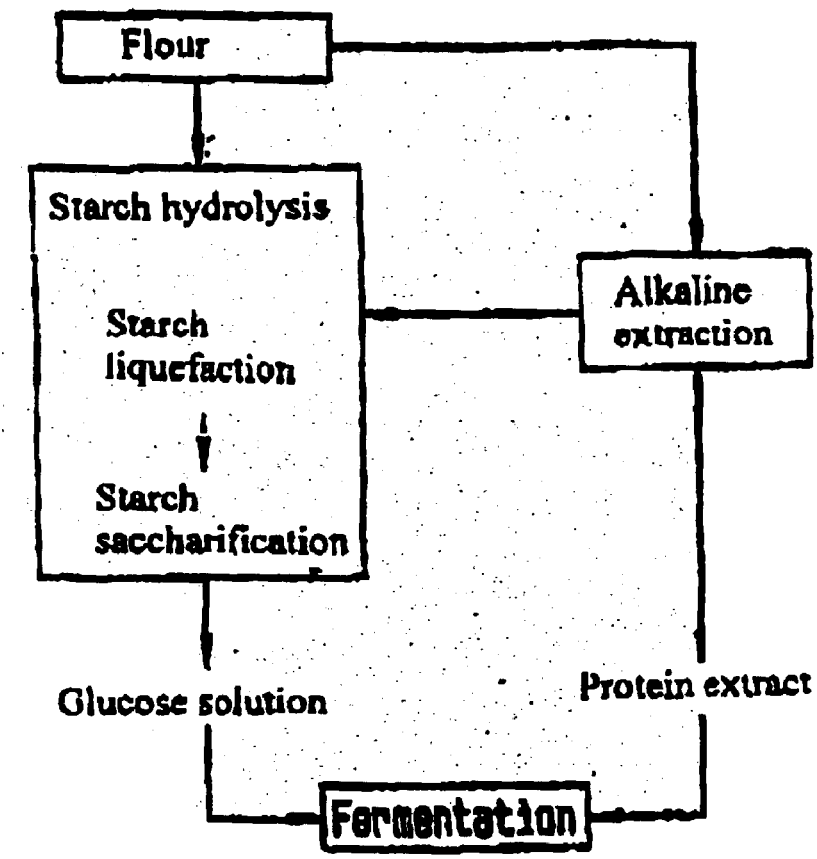

This application is the U.S. national Phase of international patent application PCT/EP01/04482, filed on Apr. 19, 2001, and claiming priority to German patent application number 10020898.3, filed Apr. 20, 2000, hereby incorporated by reference.

The invention relates to a process for producing polylactic acid from lactic acid produced by fermentation, wherein starch-containing, agricultural products, preferably grain, is used as raw material. The invention also relates to a device for carrying out this process.

The production of polylactic acid (polylactide) has been described several times. Lactic acid bacteria require for their growth, apart from vitamins, above all nitrogen-containing materials, such as amino acids and peptides. Yeast extract and peptone have proved worthwhile as a source of these substances. The MRS nutrient solution recipe proposed on the basis of J. C. De Man et al. (J. Appl. Bacteriol. 23 (1960), 130–135) is being used in the meantime in all laboratories of the world for the cultivation of lactic acid bacteria. However, the proportion of yeast extract and peptone in the medium has to be significantly increased for ensuring cell concentrations >10 g/l (Amrane, A. et al.: World J. Microbiol. & Biotechnol. 14 (1998), x-y). Both feed materials thus become cost factors in technical applications. Hence, in a continuous production plant with cell retention, the expense for yeast extract alone may account for up to 38% of the operational costs (Tejayadi, S. and Cheryan, M.: Appl. Microbiol. Biotechnol. 43 (1995), 242–248). One possibility for reducing cost is seen in that in a two-stage process, first of all a growth promoter-rich and then a low-growth promoter nutrient solution is used (Olmos-Dichara, A. et al.: Biotechnol. Lett. 19 (1997), 709–714). However, the best alternative for this is the substitution of expensive yeast extract and peptone preparations with cheaper growth promoter sources. In the literature, inter alia, whey protein concentrate (Bury, D. et al.; Int. Dairy J. 8 (1998), 149–151) and autolysate from brewery yeast (Selmer-Oisen, E. et al.: Milchwissenschaft [Milk science] 53 (1998), 367–370) are proposed for this. Shamala, T. R. et al. (Enzyme Microb. Technol. 9 (1987), 726–729) achieved satisfactory results using wheat bran hydrolysates in the low productivity range of discontinuous fermentations. The use of non-hydrolysed neutral wheat bran extracts on the other hand brought considerably poorer results. Wheat flour hydrolysates have also been investigated for their suitability as a growth promoter source (Hofvendahl, K. et al.: Enzyme Microbial Technol. 20 (1997), 301–307). However, it thus emerged that the supply of yeast extract was nevertheless necessary to achieve high productivities.

In one production process (PCT WO 98/28433), whey protein is introduced into the fermenter and hydrolysed there with the aid of proteases. A further process (PCT WO 98/212611) uses maize source water and grain gluten filtrate as growth promoter source, but wherein the addition of hydrogen peroxide is necessary to neutralise the $SO_2$ proportion present therein.

In a further work (Payot, T. et al.: Enzyme Microb. Technol. 24 (1999), 191–199), a bacterial extract from the biomass of *Bacillus coagulans* is used for the partial substitution of yeast extract For this purpose, after completing batch fermentation, the bacterial cells formed are separated off by centrifuging, washed and destroyed in a ball mill. The homogenisate obtained is then hydrolysed at 90° C. for 2 hours with addition of 6 n sulphuric acid, then neutralised with 6 n ammonia solution and freed of solid portions by centrifuging. The solution is worked up to form a concentrate by spray drying.

This procedure hides the disadvantage that, in addition to fermentation, a separate process for producing the bacterial extract is necessary and that for the procedure indicated, greater quantities of sulphate and ammonium ions pass into the fermentation medium via the extract, which, during working up to form highly pure lactic acid, have to be removed again from the latter by expensive measures.

U.S. Pat. No. 5,247,059 describes a process for producing purified lactide and lactide polymers. According to the above-mentioned U.S. patent, the starting point is lactic acid, which has been recovered from the fermentation, and this lactic acid is super-concentrated to an 85% strength lactic acid using an evaporator. A prepolymer is then formed and the polylactic acid obtained having a molecular weight of 100 to 5,000 is supplied to a lactide reactor, as a result of which lactide is obtained as crude product. This lactide is purified (>99%) and then subjected to ring-opening polymerisation.

The disadvantage of this process is that the starting point is a mere 15% strength lactic acid and that the molecular weight which can be achieved using this process is still inadequate.

Starting from this, the object of the present invention is to propose a novel process and a corresponding device, with which polylactide having a high molecular weight may be produced continuously in high yields.

This object preferably is achieved by the characterizing features of the present invention. Advantageous embodiments and further developments of the solution will be apparent from the description of the invention provided herein.

According to the invention, the biologically degradable polylactide is thus recovered by polymerisation of the cyclic dimer of lactic acid. The lactic acid originates from a fermentation process, the starting material of which is starch-containing agricultural products, in particular grain.

The process thus consists of a biotechnology process part with hydrolysis, fermentation and purification of the lactic acid by membrane technology and a section comparable to polymerisation processes.

The starting material is flour, in particular rye flour, or more precisely the starch present therein. The hydrolysed starch is degraded enzymatically to form glucose and fermented to form aqueous lactic acid. The lactic acid then has to be purified and concentrated, before it may be polycondensed to form a first prepolymer. This prepolymer is depolymerised under suitable conditions to form the actual starting material of polymerisation, the cyclic dimer of lactic acid (dilactide).

The dilactide may now be polymerised to form the polylactide under the influence of a catalyst (for example tin octoate) and with the aid of the hydroxyl groups acting as starting centres. However, the quality of the polymer depends quite crucially on the purity of the dilactide used, which is why rectifying purification of the dilactide is necessary before ring-opening polymerisation.

The subsequent demonomerisation of the polylactide melt should prevent premature degradation processes in the end product.

An essential element of the invention is the recovery of highly pure lactic acid by continuous high-performance fermentation. This part of the process is described more precisely below.

Mixing of flour, preferably rye flour, and deionised water, is at the start of the process. This may take place in a simple stirred vessel. Careful stirring and avoiding high water temperatures is important, since otherwise rising steam could gelatinise with the flour or form lumps. According to current practice, it was imperative to add external growth promoter sources, preferably peptone and yeast extract, in considerable quantity in continuous high-performance fermentations. The costs incurred for this put the economic viability of such processes in question. In addition, with addition of such sources, Interfering foreign material, for example foreign ions, (in particular chlorides) are entrained, which make purification of the sodium lactate formed or the lactic acid by membrane separation processes very difficult and additionally reduce the yield of polylactide in a subsequent polymerisation process to uneconomic viability with inadequate purification. Contrary to current practice, according to the process of the invention, in process step a) no external growth promoter source, such as yeast extract or peptone, is used, but the growth promoter source is recovered from the starting material itself, namely the grain. The growth promoters (peptides, amino acid, vitamins, salts), which the lactic acid bacteria require during fermentation in addition to a usable carbon source, thus originate from the starting material according to the invention.

Surprisingly, it has been found that alkaline protein extracts from flour or bruised grain already represent a valuable replacement for peptone or yeast extract, when an additional hydrolytic cleavage by proteinases is dispensed with. The effect may be increased further in that the excess biomass formed is specifically lysed in the process, as a result of which certain essential growth promoters are released again or additionally. Both peptone and yeast extract may be completely dispensed with in this manner in high-performance fermentations.

If grain is used as raw material, protein extraction may be coupled with the starch hydrolysis process. There is the possibility of using a partial quantity of the flour or bruised grain for recovering the extract and introducing the starch fraction thus remaining into the liquefaction phase of hydrolysis. An alternative to this is alkaline extraction of the residual solid generally being produced in starch hydrolysis and which is separated off from the hydrolysate.

Lysis of some of the biomass situated in the fermentation system must take place as completely as possible and so that no damage thus occurs to the active cell fraction required for maintaining the fermentation process. Some of the biomass from the fermenter is thus circulated, lysed there and the lysate obtained returned again to the fermenter. In addition, it is possible to separate off the excess biomass and to lyse outside the fermentation system and return the extract thus obtained to the fermentation system.

The lactic acid recovered in this manner is then subjected to ultrapurification, as already stated in the introduction, and subsequently then concentrated and subjected to polymerisation.

The invention also relates to a corresponding device for carrying out the process.

The invention is illustrated in more detail below using figures and exemplary embodiments.

Figure 2:
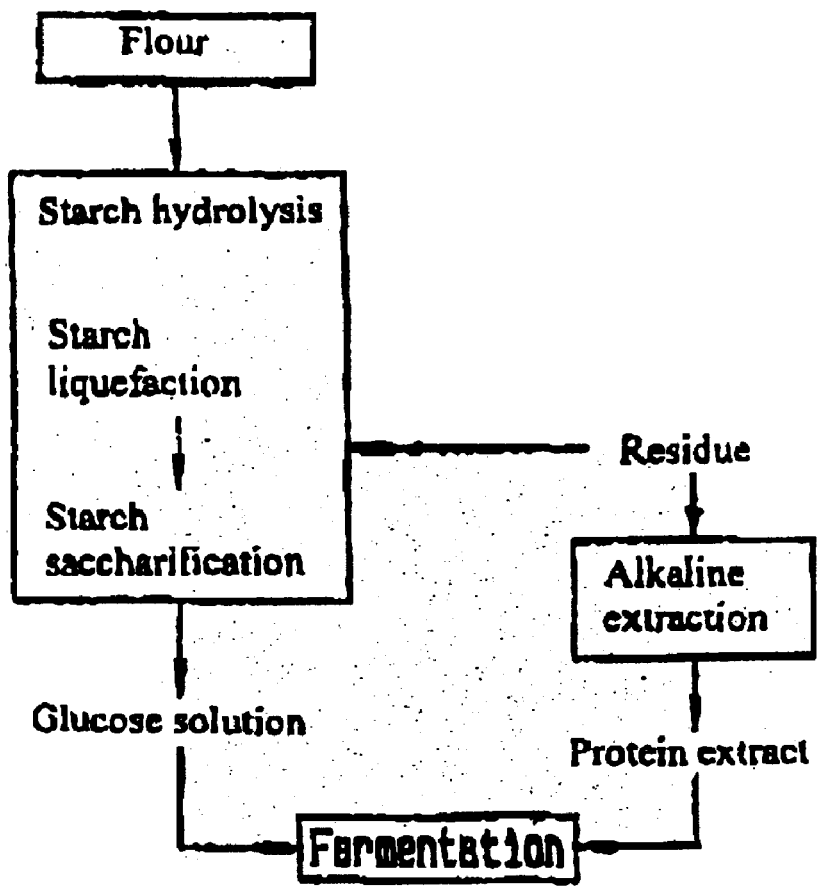
Figure 3:
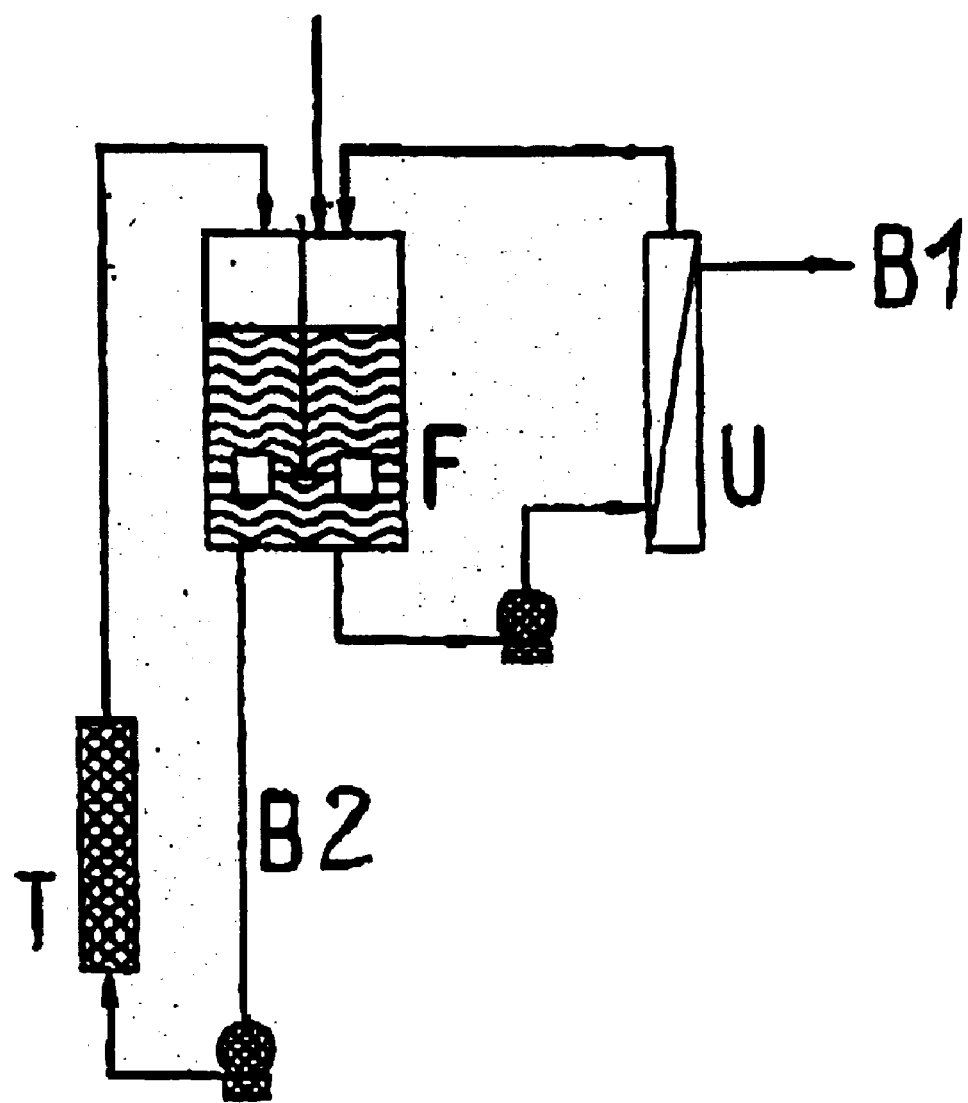
Figure 4A:
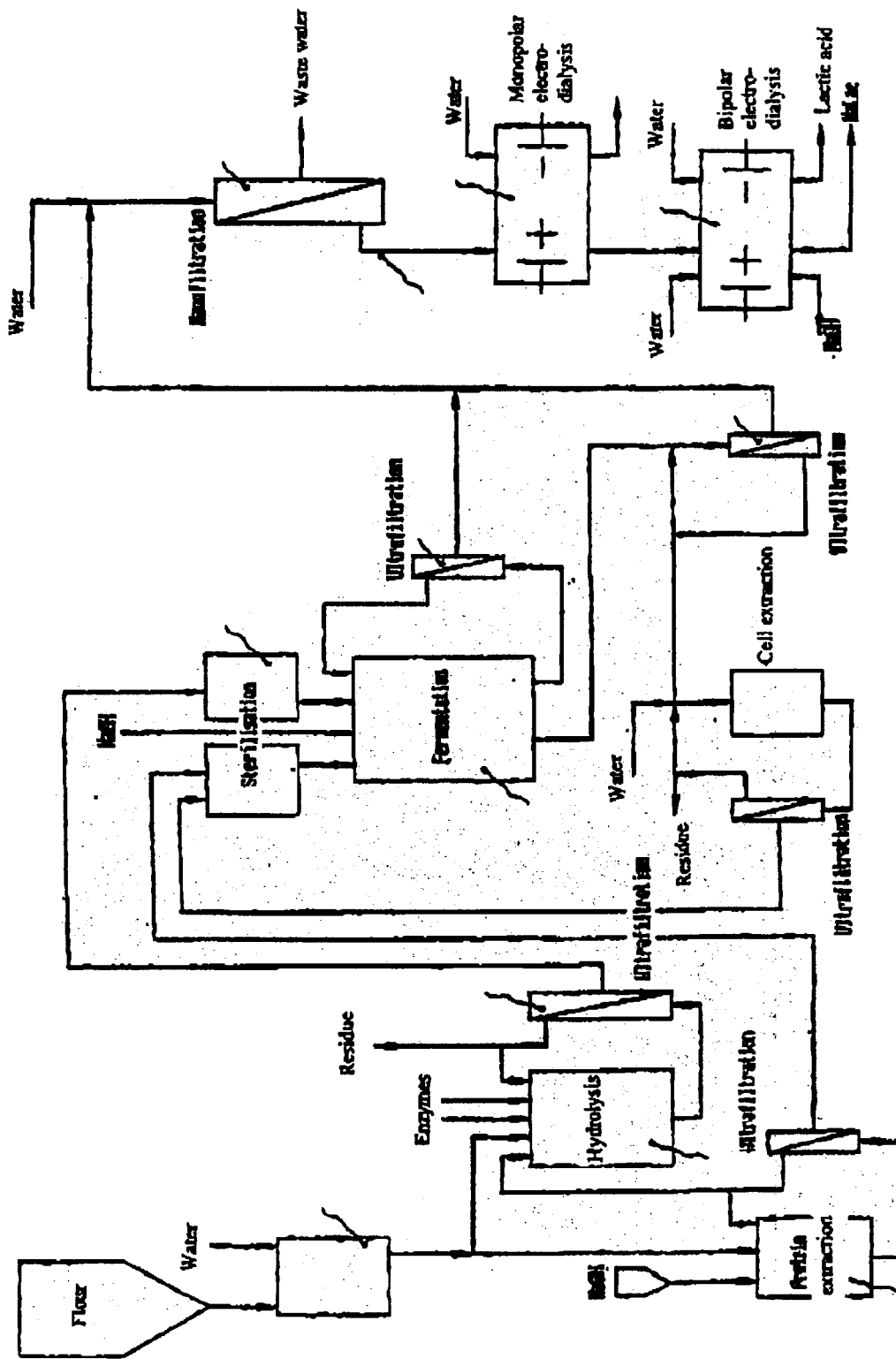
Figure 5:
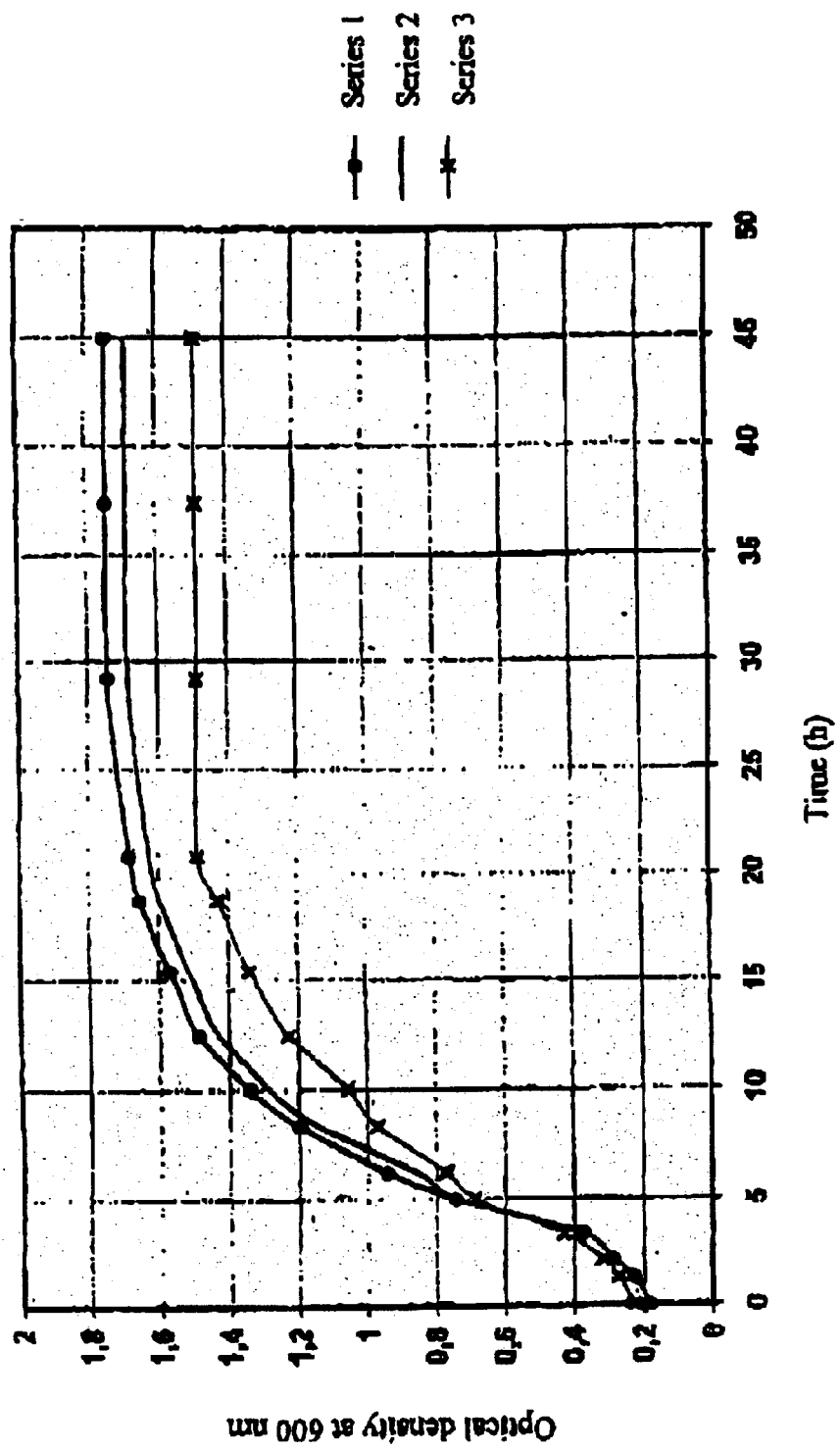
Figure 6:
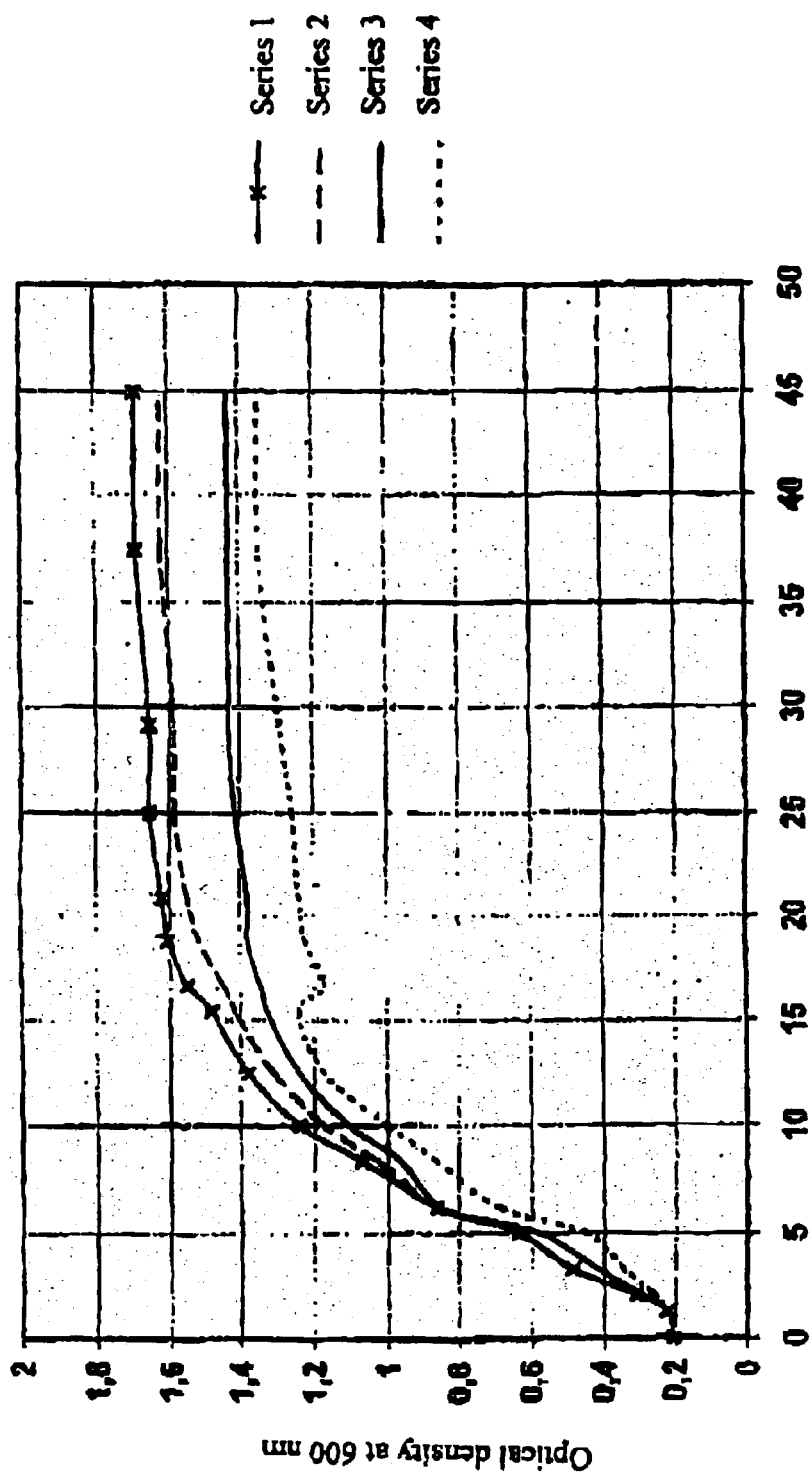
Figure 7:
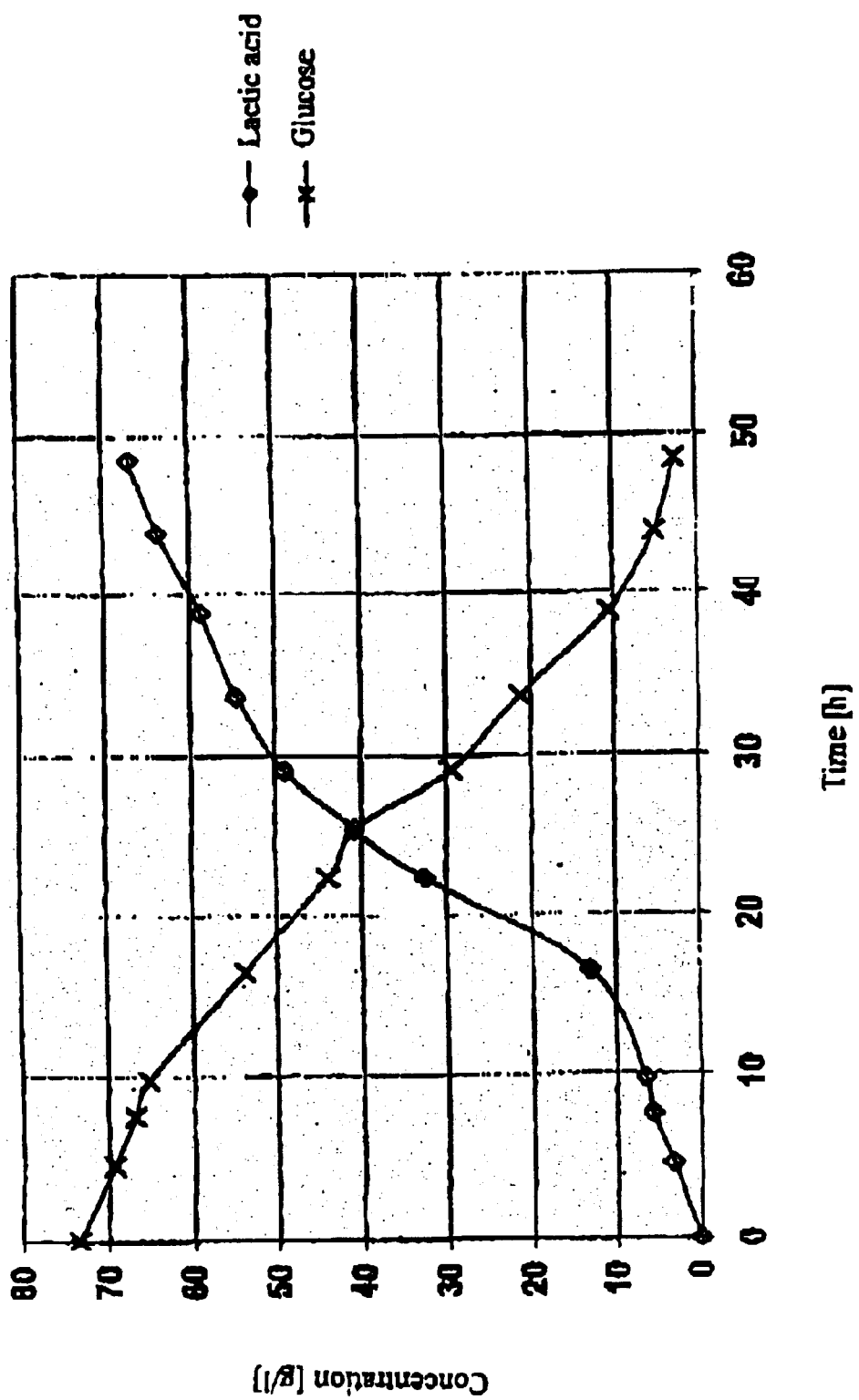

FIG. 1 shows the scheme of protein extract production from flour/bruised grain,

FIG. 2 shows the scheme of protein extract production from residues of starch hydrolysis, FIG. 3 shows process scheme of continuous fermentation with bacterial extract production, FIGS. 4a and b show the schematic process path of a complete device for producing polylactide, FIG. 5 shows growth of *Lactobacillus rhamnosus* 4759 in peptone-free MRS medium with addition of alkaline rye protein extract (2) compared to the growth in MRS medium (1) and MRS medium without peptone (3), FIG. 6 shows growth of *Lactobacillus rhamnosus* 4758 in yeast extract-free MRS media with addition of bacterial extracts of different concentrations (produced from cell suspensions with dry biomass contents of 15.7 g/l (3) or 78.4 g/l (2) compared to the growth in MRS medium (1) and MRS medium without yeast extract (4), FIG. 7 shows substrate and product concentrations of batch fermentation of. *Lactobacillus paracasei* 160111 on rye flour hydrolysate with addition of protein extract from rye flour and bacterial extract from separate biomass.

FIG. 1 shows in a scheme, protein extract production from flour and bruised grain. Some of the flour or bruised grain is then supplied directly to alkaline extraction for extract recovery and then the protein extract obtained is transferred to the fermenter for fermentation. It is thus preferable that one tenth to one half, preferably one quarter, of the flour is supplied to alkaline extraction and the remainder is used in starch hydrolysis.

An alternative to this is the alkaline extraction of the residual solid generally being produced during starch hydrolysis, which is separated from the hydrolysate (FIG. 2).

FIG. 3 shows a process scheme of continuous fermentation with bacterial extract production. In a fermentation system, which consists of a fermenter F and an ultrafiltration module U situated in the external circuit, the biomass is retained and gradually enriched in the system. Since an optimum concentration for the active biomass has to be adhered to for effective lactic acid production, it is normally compulsory, in addition to the filtrate outlet B1, to also provide a second outlet B2. The latter serves to remove the excess cell mass from the fermenter. This second starting material stream is utilised according to the invention for recovery of cell extract, in that it is passed over a thermal hydrolysis stage T, where the cells are destroyed by thermolysis. The lysate is then returned to the fermenter after cooling. In addition, there is the possibility of adding lysating enzymes to this material stream; before the thermal treatment or to execute lysis with the aid of radiation, in particular microwave radiation.

The procedure of the invention at the same time also offers a novel possibility for maintaining We concentration of the active biomass in the reactor at optimum level, when appropriate control systems (for example a suitable clouding sensor) ensures that precisely only so much biomass is lysed in the unit of time, as has grown in the same time period. In this case, the lysate stream is freed of the remaining solid portions from fermentation, for example by filtration, before returning to the fermenter.

Figure 4B:
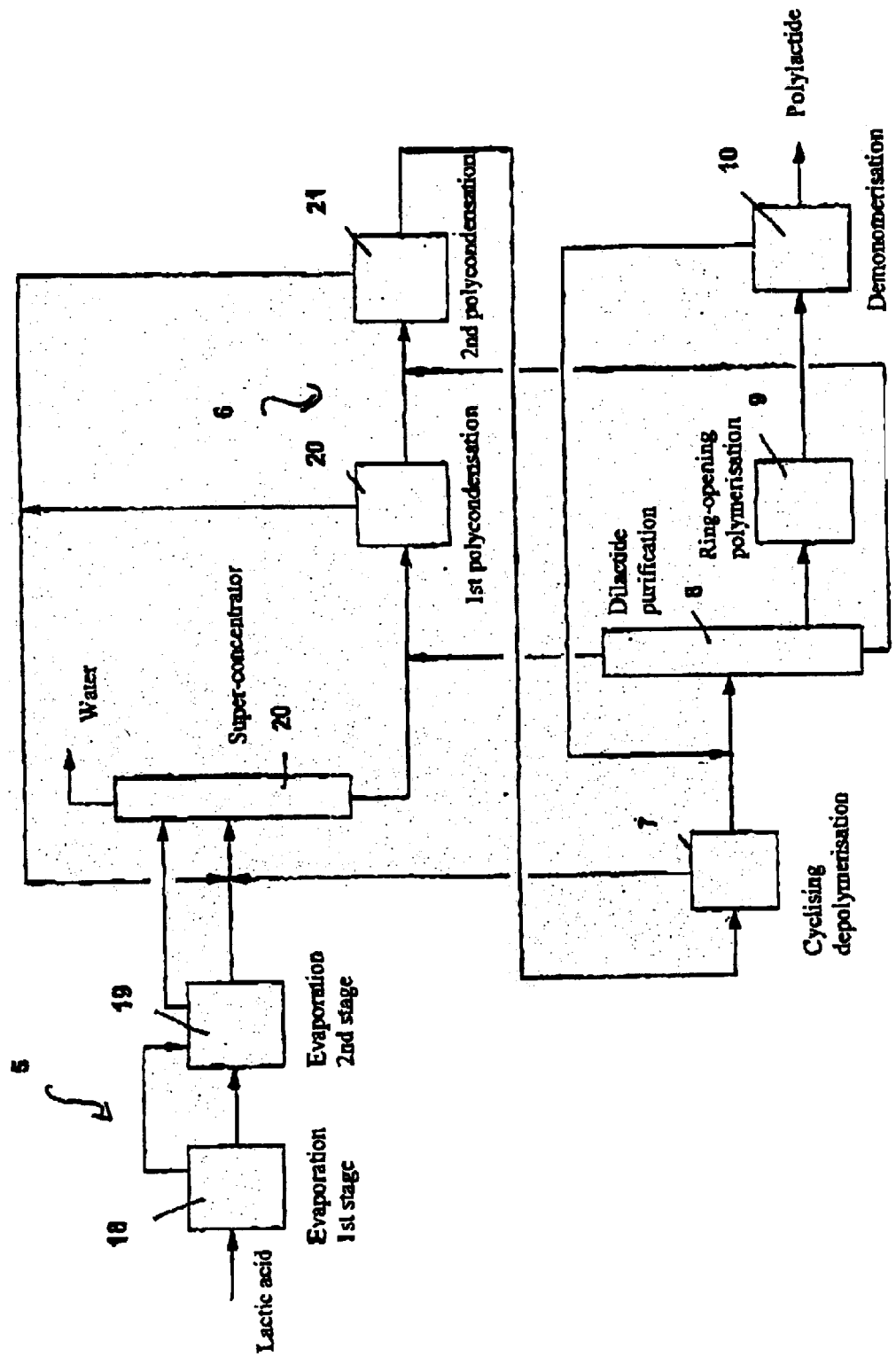

FIG. 4 shows schematically the process path of production.

At the start of the process, mixing of flour, preferably rye flour, is in a mixing device 1. According to the invention, some, preferably about one quarter, of the suspension thus produced is thus supplied to continuous protein extraction 11, about three quarters flow directly into the hydrolysis device 2. The latter may be arranged to be discontinuous or continuous. In the discontinuous case, it is operated as it were continuously by upstream and downstream buffer containers.

Hydrolysis is a two-stage enzymatic process. In the first stage, the starch is liquefied with addition of the endoenzyme α-amylase at 80° C. for two hours. Cleavage of the hydrolysed starch then takes place with the aid of the exoenzyme glucoamylase at 55° C. The second step lasts about four hours and is carried out in a separate reaction stage. Total saccharification of the starch present in the rye flour is thus achieved. Simple, heatable stirred vessels may be used as apparatuses.

The hydrolysate is separated from solids in a filter press and supplied to fermentation. The separated biomass is residue and may be used as fodder or possibly for biogas production.

In protein extraction in extractor 11, the flour-water suspension is kept at a pH value of 10 with addition of sodium hydroxide solution for a period of eight hours. The protein fraction is thus dissolved and may be skimmed off as permeate in subsequent ultrafiltration 30 and added to the fermenter. The filter cake is neutralised using lactic acid and hydrolysed. Pressure and temperature correspond to the ambient conditions. Since the mixture has to be stirred, the container should be a stirred vessel.

Further growth promoters required, such as inter alia, amino acids and vitamins, may be recovered by induced lysis from the ultrafiltrated biomass being produced in fermentation 3. This is carried out using ultrafiltration device 12. The induced lysis may take place in different ways, here it consists of 20-minute heating at 95 C in a heated container. Ultrafiltration separates the biomass from the cell extract, which flows back into fermentation 3. The biomass being produced may in turn be utilised as fodder.

Before the nutrient and protein extract as well as the hydrolysate pass to fermenter 3, they have to be sterilised briefly (20 minutes) at 120° C. (minimum temperature 110° C.) using sterilisers 13. Hydrolysate and growth promoter extracts may not be sterilised together in order to avoid the so-called Maillard reactions taking place at these temperatures between nitrogen compounds (proteins) and glucose, which in particular cause undesirable discolouration. The containers 13 have to be designed for the residence time and temperature for sterilisation.

Fermentation is the process stage in which bioconversion of glucose into lactic acid takes place. This takes place in the lactic acid bacterial cells according to a complicated path of many metabolic intervention reactions (glycolysis), each of which is catalysed by a certain enzyme. It is an anaerobic process, in which the bacteria form lactic acid in order to recover the energy necessary for their reproduction. The microbial reaction thus also provides, in addition to the lactic acid, cell mass and other products in very low quantities.

The activity of the bacterial cells depends on a series of process parameters, (temperature, pH value, osmolality, substrate concentration, growth promoter availability etc.). The optimum temperature is 33° C. and the pH value 6.0 for the selected strain of *Lactobacillus paracasei*. The addition of sodium hydroxide solution is necessary to regulate the pH value. Lactic acid in the form of sodium lactate is produced under these conditions. The residence time is typically between one-and-a-half and four hours (throughflow rate: 0.25–0.67). Care must be taken in fermenter 3 that in the interior it has as smooth as possible a surface free of corners, edges and grooves, so that the regularly necessary sterilisation of the fermenter may be kept simple and effective (steam purification). A stirring mechanism is required.

The fermenter content is ultrafiltrated continuously, wherein sodium lactate is produced as permeate. The cell-containing retentate flows back into the fermenter 3. In order to prevent concentration of the cell mass, a second product stream leaves the fermenter 3. The sodium lactate present therein is recovered in a farther ultrafiltration stage 31, the cell-containing retentate does not flow into the fermenter, but into nutrient extraction already described above.

Ultrapurification of the lactic acid is essential in the process of the invention (feature b). This is required, since the ultrafiltrated fermenter outlet contains, in addition to lactic acid in the form of sodium lactate, further components which in particular sensitively disturb the later polymerisation and thus may even bring the entire process to a standstill. Above all inorganic and organic acids, (acetic acid, propionic acid, sulphuric acid, hydrochloride acid) and their salts, mono-, di- and oligosaccharides and dyestuffs, should be mentioned as undesirable contents.

The chloride ions should primarily be separated from the sodium lactate with he aid of nanofiltration 15. Chloride ions are introduced into the process mainly with the enzymes used for hydrolysis. They are not only very disturbing in the polymerisation reactions, but also severely attack the container materials. Up to 98% of the chloride ions may be retained by the membrane used.

In addition, further ions, such as sulphates and phosphates, permeate through the membrane, the sodium lactate remains in the retentate.

Monopolar, just like bipolar, electrodialysis 16 is a discontinuous process. In order to nevertheless facilitate continuous lactic acid production, two dialysis plants are operated alternately.

Monopolar electrodialysis is used for two reasons:
1. Separation of the non-ionic from the ionic components and
2. Concentration of the sodium lactate.

The non-ionic components, which are separated from the sodium lactate, include in particular nitrogen and phosphorus compounds. These materials can be found in the large quantity of waste water being produced and prevent complete return of this quantity of water to hydrolysis and fermentation. Temperature and pressure are as for ambient conditions.

In order to finally recover lactic acid from the sodium lactate, electrodialysis 17 with bipolar membranes is used. The plant has three circuits:
a salt circuit, into which the sodium lactate enters,
a lye circuit, into which the sodium ions diffuse and are joined to hydroxide ions to form sodium hydroxide solution
and an acid circuit, in which lactate ions are joined to protons to form lactic acid.

In order to keep the stream requirement of electrodialysis 17 within economic limits, it is operated so that not all of the sodium lactate is converted to lactic acid. This residual quantity must be ejected from the process. The sodium hydroxide solution produced flows back into fermentation, in order to regulate the pH value there.

The temperature of the circulating solutions should be kept constant at 33 C. The intermediate storage containers thus have to be cooled.

The lactic acid coming from bipolar electrodialysis 17 must be concentrated further (feature c). According to the invention, two-stage evaporation of lactic acid is carried out with evaporator 18, 19. The aqueous lactic acid is thus first of all boiled at excess pressure, as a result of which a large part of the water already evaporates. This steam may then be utilised as heating medium in order to expel further water from the remaining lactic acid at lower pressure. The liquid then still remaining is concentrated (super-concentration) in a Roberts evaporator 20 with attached three-plate rectification column to give 90% strength, preferably 95% strength lactic acid.

The concentrated lactic acid is now polycondensed to form a prepolymer in two reactors 20, 21 with external circulating evaporator and with addition of a catalyst. Pre-condensation takes place at two different pressures. In the first reactor 20, ambient pressure or even slight excess pressure prevails, in order to prevent evaporation of the lactic acid. If the larger part of the lactic acid is polycondensed to form a high-boiling oligomer, the reaction may be continued in the second reactor 21 under vacuum (50 mbar). The vacuum applied facilitates evaporation of the water being produced in the reaction from the melt and thus prevents the reaction being brought to a standstill by reaching the chemical equilibrium. The residence time in the reactors is three to four hours, the temperatures are 180 C and 190 C, in each case in the first and second reactor. The prepolymer has a molecular weight of 3,400 g/mole (2,500–4,000 g/mole).

Depolymerisation (feature d)) to form the actual monomer of polylactide, the dilactide, preferably takes place in a falling-film evaporator 7. The prepolymer is distributed over several heated vertical pipes and trickles down therein in a thin film. The temperature is increased to about 210° C. and the negative pressure from pre-condensation retained (50 mbar). The increased temperature accelerates dilactide formation, the vacuum and the thin falling film (<1 mm) ensure rapid evaporation of the resulting dilactide. The falling-film evaporator 7 is operated as a circulating evaporator in order to ensure complete wetting of the heated surface.

The vapour-like product stream of the falling-film evaporator 7 is immediately partly condensed. Temperature and pressure of partial condensation are thus selected so that the water present in the vapour and as large as possible a part of the lactic acid remains like vapour. The dilactide is almost completely condensed. The condensate still contains only a low quantity of lactic acid and oligomers, such as for example lactoyl lactic acid, the linear dinner of lactic acid Together the important hydroxyl group concentration, which is typically 57 meq, is produced therefrom.

In ring-opening polymerisation, the achievable molecular weight, and thus important mechanical properties of polylactide, depends on the dilactide purity. Hydroxyl groups are present in the dilactide due to the residual lactic acid and lactoyl lactic acid. They are starting centres of polymerisation. The higher the concentration of hydroxyl groups in the dilactide, the more polymer molecules are produced and the lower the achievable molecular weight. The required hydroxyl group concentration is 20 meq, which leads to a theoretical molecular weight of 50,000 g/mole. The maximum achievable dilactide purity using this column is 10 meq.

The concentration of hydroxyl groups in the dilactide is still too great after cyclising depolymerisation. The condensed dilactide is purified to the required hydroxyl group concentration in a rectification column 8 with ditch. At the same time, the column may be utilised to control the molecular weight.

The contaminated dilactide enters the upper part of the column and leaves it purified in the lower part as vapour-like ditch. The dilactide vapour is condensed before it enters the ring-opening polymerisation reactors. Top product (148° C., 30 mbar) is the residual lactic acid, the higher boiling oligomers of lactic acid and other contaminants possibly present are removed via the bottom (172° C., 60 mbar). The column is operated under vacuum (30–60 mbar) from thermodynamic points of view (avoiding too high temperatures improving the relative volatilities).

Ring-opening polymerisation (feature f)) takes place in a stirred vessel cascade 9 of two reactors with addition of a catalyst The concentration of the catalyst is thus kept comparatively low (5*10-5 mole catalyst/mole dilactide, concentration range: 2*10-4 to 2*10-5 mole/mole), in order to obtain high molar weights and to repress side reactions. The reactors are at atmospheric pressure.

Ring-opening polymerisation is an exothermic reaction. In order to avoid temperatures above 240° C. (thermal degradation, side reactions), some of the resulting heat of reaction must be removed. This takes place in the first reactor by adding sub-cooled dilactide: the dilactide is thus sub-cooled so far that a temperature of 200° C. is adjusted in the first reactor. About 70 percent of the dilactide thus polymerises for a residence time of 2.5 hours.

The second reactor is operated adiabatically and the residence time selected (2 hours) so that the dilactide conversion is finally 90 percent. The melt temperature thus rises to 215 C.

The polylactide now has the required molecular weight of about 50,000 g/mole. However, about mine percent of monomer is still present in the melt. However, a polylactide which is stable over a longer time should contain no more than one percent dilactide. Demonomerisation should thus be carried out. This in turn is made more difficult by the fact that ring-opening polymerisation is an equilibrium reaction. At temperatures around 200° C., the equilibrium concentration of dilactide is about five percent. Demonomerisation must thus be effected either very quickly to minimise re-formation of dilactide, but this is very difficult to effect at the high viscosities. A second possibility which is used here consists in blocking the catalyst by adding a stabiliser (for example α-tropolone, see patent specification German Patentschrift 19 537 364) and to almost bring the reaction to a standstill and thus avoid damaging re-formation of dilactide.

In the present process, demonomerisation (feature g)) takes place in two separate apparatuses 10 after adding the stabiliser. In the first apparatus, the melt is let down to a pressure of 10 mbar, wherein the greater part of the monomer evaporates. The dilactide content may thus be reduced to approximately 2%. However, the temperature thus also falls to 195 C, which leads to a viscosity increase to about 700 Pa*s. In order to finally also evaporate the last two percent of dilactide from the highly viscous melt, the pressure in the second apparatus, the so-called finisher, is reduced to 2.5 mbar.

Before the melt is demonomerised further, it experiences a temperature increase in order to prevent too high viscosities at the outlet of the finisher. The finisher consists of a cylindrical reactor sleeve, which is filled to 20–30% of its volume with polymer melt. A basket-like support, to which vertically standing annular discs are attached, rotates around the cylindrical axis. The discs dip into the melt with part of their surface. The highly viscous melt is drawn by the discs due to rotation and exposed to the vacuum in the form of a film. The principle of a suitable finisher is described, for example in U.S. Pat. No. 5,779,986.

Instead of such a "lying" finisher, a so-called thin-layer evaporator is also suitable. Here, the melt to be demonomerised flows down on the inner wall of a vertically standing, externally heated pipe. A driven shaft, which carries wiping elements, which brush the melt over the heated surface during flowing down to form a thin film, rotates in the pipe axis. The formation of thin layers and their constant renewal facilitate evaporation of the monomer.

A constantly renewing, very large surface, which is necessary for demonomerisation to 0.5 percent monomer content, is obtained using the devices indicated by way of example. The temperature of the melt thus drops to 190° C. and the viscosity rises to about 1,440 Pa*s.

EXAMPLE 1

1 kg of rye flour in 5 litres of water are stirred in a 10-litre stirred fermenter with simultaneous adjustment of the pH value to 10.0 (addition of 3N NaOH solution). After a stirring period of 2 hours at 20° C., separation of the starch-containing solid fraction takes place by filtration. The aqueous supernatant is added to the fermentation medium as alkaline protein extract.

The effectiveness of this protein extract can be illustrated by the growth behaviour of the strain *Lactobacillus rhamnosus* 4759 in microtitre plates of the apparatus system Bioscreen (Messrs. Labsystems, Finland). For this purpose 0.24 ml of a glucose-MRS medium, which contained no peptone, was treated with 0.1 ml of the protein extract produced and inoculated with 0.01 ml of an 18-hour culture of the afore-mentioned strain and cultivated under standard conditions (T=33° C., pH=6.0). A full MRS medium and an MRS medium without peptone were used as control batches. FIG. 5 shows the growth curves of *Lactobacillus rhamnosus* 4759 on the three media described. The growth curves (1) and (2) differ only slightly, that is that in this case, the protein extract may be regarded as a complete replacement for peptone.

EXAMPLE 2

Cell mass of *Lactobacillus rhamnosus* is separated off from fermented fermenter liquid by centrifuging and resuspended in water so that cell suspensions having dry biomass contents of 15.7 g/l and 78.4 g/l are produced. The latter are heated at 60° C. for 20 minutes to lyse the cells. After cooling to about 30° C. and separation of the cell wall residues, the clear solution is added to the fermentation medium as bacterial extract.

The effectiveness of this bacterial extract can be illustrated by the growth behaviour of the strain *Lactobacillus rhamnosus* 4759 in microtitre plates of the apparatus system Bioscreen (Messrs. Labsystems, Finland). For every 0.24 ml of an MRS medium without yeast extract, in each case 0.1 ml of one of the two bacterial extracts and 0.01 ml of an 18-hour pre-culture of the afore-mentioned strain were added and incubated at T=33° C. and pH=6.0. A full MRS medium and an MRS medium without yeast extract served as control batches. FIG. 6 shows the growth curves of *Lactobacillus rhamnosus* 4759 on the four media mentioned. The growth curves (1) and (2) differ only slightly, that is that in this case, the bacterial extract may be regarded as a complete replacement for yeast extract.

EXAMPLE 3

29 litres of enzymatically recovered rye starch hydrolysate (glucose content: 120 g/l) were internally sterilised in a 50-litre stirred fermenter. The addition of 10 litres of the protein extract produced according to Example 1, 6 litres of the bacterial cell extract produced according to Example 2 and 1 litre of an aqueous solution, which contained 96 g of dipotassium hydrogen phosphate, 4.8 g of magnesium sulphate and 2.4 g of manganese sulphate, then took place under aseptic conditions, 2 litres of a pre-culture of the strain *Lactobacillus paracasei* 160111 served as inoculum. The temperature was kept constantly at 33 C and the pH value at 6.0 during the subsequent fermentation process. 30% strength sodium hydroxide solution served as correcting agent for pH regulation.

After 48 hours, the glucose used was completely spent and converted to lactic acid (FIG. 7).

EXAMPLE 4

A salt nutrient medium, which contained, inter alia, 50 g/l of glucose, 10 g/l of yeast extract and 10 g/l of peptone, was metered at a constant rate into a 5-litre fermenter, which was coupled to an ultrafiltration module in the external circuit. The same quantity of liquid left the fermentation system at the same time as cell-free sodium lactate solution via the outlet of the ultrafiltration unit. In Table 1, the productivities of lactic acid production determined at different throughflow rates using the strain *Lactobacillus paracasei* 160111 are compared to the productivities which were obtained under otherwise the same conditions using a nutrient solution, which consisted of 10% protein extract according to Example 1 and contained 50 g/l of glucose and 10 g/l of yeast extract.

EXAMPLE 5

A salt nutrient medium, which contained, inter alia, 40 g/l of glucose, 10 g/l of yeast extract and 10 g/l of peptone, was metered at a rate of 6 l/h into a 50-litre fermenter, which was coupled to an ultrafiltration module in the external circuit. The fermentation medium circulated constantly between fermenter and ultrafiltration module, where the same quantity of liquid left the fermentation system at the same time as cell-free sodium lactate solution. The lactic acid productivity achieved at the throughflow rate of $D=0.12\ h^{-1}$ using the strain *Lactobacillus paracasei* 160111 was 4.0 g/lh.

EXAMPLE 6

A rye hydrolysate-salt nutrient medium, which consisted of 20% rye protein extract according to Example 1 and contained 40 g/l of glucose, was metered at a rate of 6 l/h into a 50-litre fermenter, which was coupled to an ultrafiltration module in the external circuit. The fermentation medium circulated constantly between fermenter and ultrafiltration module, where the same quantity of liquid left the fermentation system at the same time as cell-free sodium lactate solution. Compared to Example 4, the fermentation regime was changed so that the biomass which had grown in the course of the process beyond the required concentration of 20 g/l was heated in a second circuit for 5 minutes at 80° C. and then returned again to the reactor system as lysate. In the present case, the biomass growth in the fermenter was 2 g/lh so that in each case 4.5 litres, which contained about 100 g of biomass, were taken hourly from the fermenter system and lysed in the manner described. The lactic acid productivity achieved at the throughflow rate of $D=0.12\ h^{-1}$ using the strain *Lactobacillus paracasei* 160111 was 3.95 g/lh.

EXAMPLE 7

A rye hydrolysate-nutrient medium, which consisted of 20% rye protein extract and contained 50 g/l of glucose, was metered at a rate of 12.5 l/h into a 50-litre fermenter, which was coupled to an ultrafiltration module in the external circuit. In this case, a rye protein extract was used, the active ingredient portion of which was twice as high as that of the extract produced according to Example 1. In this case, not flour but the starch-free residue from starch flour hydrolysis served as starting material, wherein the solid-water ratio during extraction was twice as high as in Example 1. The fermentation medium circulated constantly between fermenter and ultrafiltration module, where the liquid volume corresponding to the metered quantity left the fermentation system at the same time as cell-free sodium lactate solution.

The biomass concentration in the reactor system thus remained constant at about 30 g/l, that a partial stream of the fermentation liquid, which was controlled via a flow-injection clouding measurement, was passed constantly over the thermal lysis path (T=100° C.) and after separation of the cell residues, was returned again to the fermenter with the aid of a filtration device integrated into the process.

The lactic acid productivity achieved at the throughflow rate of D=0.25 h$^{-1}$ using the strain *Lactobacillus paracasei* 160111 was 13.5 g/lh.

EXAMPLE 8

The cell-free sodium lactate solution from Example 7 must now be purified of foreign material and converted to lactic acid. Care has thus already been taken with the input materials to ensure that the load of foreign materials is minimal. Hence, the concentration of sulphate ions in the fermentation medium can be reduced from 286 g/l to 86 g/l by using magnesium oxide instead of magnesium sulphate and lactic acid instead of sulphuric acid. The introduction of chloride ions into the process takes place mainly due to the enzyme Termamyl 120 L. The chloride content may be reduced here from originally 675 g/l to 212 g/l with the aid of an ion exchanger.

Most of the remaining chloride ions are separated from the sodium lactate solution in nanofiltration following ultrafiltration. Nanofiltration is operated as three-stage diafiltration. The chloride ions diffuse through the membrane, the lactate ions remain in the retentate. The chloride concentration of 0.892 g/l in the culture filtrate is reduced in this manner to 0.003 g/l in the concentrate of the third nanofiltration stage.

The subsequent monopolar electrodialysis serves for concentration of the sodium lactate solution and deposition of the non-ionic components. In particular, most of the residual sugar (reducing and non-reducing mono-, di- and oligosaccharides) remains in the diluate. The total phosphorus concentration may be reduced from 0.58 g/l in the feed to 0.12 g/l in the concentrate. A reduction from 1.04 g/l to 0.131 g/l is produced for nitrogen.

If the residual sugar is not completely separated from the lactic acid, the yield drops considerably during polymerisation: the remaining saccharides lead to severe carbonisation of the prepolymer during cyclising depolymerisation. Depending on the impurity, up to 50 percent of the prepolymer used may thus carbonise and thus becomes unusable.

Finally, bipolar electrodialysis converts the sodium lactate into aqueous lactic acid and sodium hydroxide solution. The latter is returned and used for pH regulation in fermentation. The lactic acid produced has a concentration of about 150 g/l. The concentration of chloride ions is less than 30 mg/l and that of sulphate ions less than 10 mg/l. The concentration of the total nitrogen and of the phosphorus lies in each case below 100 mg/l. The lactic acid consists of 95% L(+)-lactic acid and 5% D(−)-lactic acid.

EXAMPLE 9

The aqueous lactic acid from Example 8 is concentrated in two-stage evaporation with subsequent rectification. In the first stage of evaporation, the weight portion of lactic acid is increased from 0.15 to 0.4. After the second stage, it is 78 percent. The lactic acid content is finally increased to 95% in the three-plate rectification column.

The concentrated lactic acid is polymerised in two-stage polycondensation with the aid of SnCl$_2$ as catalyst to form a prepolymer having average molecular weight of 3,400 g/mole. Atmospheric pressure and a temperature of 180° C. thus prevails in the first reactor. The pressure in the second reactor is 50 mbar and the temperature 190° C.

While retaining the vacuum and increasing the temperature to 225° C., the prepolymer then depolymerises in a falling-film evaporator to form the dilactide, the cyclic dimer of lactic acid. The vapour-like product stream contains 98% dilactide, 1% lactic acid and lactoyl lactic acid and 1% water. The residual water and some of the lactic acid is separated from the dilactide by partial condensation. The condensate has a concentration of OH groups of 0.04 mole/kg. In the subsequent rectification, the residual lactoyl lactic acid and lactic acid is also separated from the dilactide in order to obtain the required purity of 0.02 mole/kg. This purity is necessary for a molecular weight of the polymer of 50,000 g/mole. Ring-opening polymerisation takes place in the two following reactors. With addition of 5 moles of tin octoate per 100,000 mole of dilactide and a temperature of 195° C., the dilactide polymerises in the first reactor to form a polylactide having an average molecular weight of 35,000 g/mole, wherein 70% of the dilactide is reacted. In the second reactor, the temperature is increased to 215° C. Ado the molecular weight to 50,000 g/mole. The conversion of dilactide rises to 90%. The two reactors are under atmospheric pressure.

In this state, the polylactide still contains 10% dilactide. In order to obtain a stable polylactide, the dilactide portion must be reduced to below one percent. This likewise takes place in two stages. In the first stage, the polylactide enters a downpipe under vacuum (10 mbar). Most of the dilactide thus evaporates, and the emerging melt still has 2% monomer. Demonomerisation to below one percent dilactide takes place in a, disc reactor, which is under a pressure of 2.5 mbar. The large surface required to evaporate the residual monomer is produced by rotating discs, which are rotated by the melt and thus convey dilactide from the melt interior to the surface.

The polylactide thus produced has a molecular weight of 50,000 g/mole, a monomer content of less than 1 percent and a melting point of about 170° C. The slightly yellowish polylactide consists of 95% L-dilactide and 5% D-dilactide.

TABLE 1

Comparison between the lactic acid formation productivities achieved with *Lactobacillus paracasei* under continuous fermentation conditions on a glucose-MRS medium and an MRS medium, in which peptone has been replaced by alkaline rye protein extract.

| | Throughflow rate (h$^{-1}$) | | |
|---|---|---|---|
| | 0.1 | 0.25 | 0.5 |
| Medium with yeast extract and peptone | 3.4 g/lh | 13.2 g/lh | 17.0 g/lh |
| Medium with protein extract and yeast extract | 3.4 g/lh | 13.0 g/lh | 16.2 g/lh |

What is claimed is:

1. Process for producing polylactic acid comprising:
    a) fermentative recovery of lactic acid from starch-containing agricultural products, wherein the growth promoters are recovered continuously from the starting material by alkaline extraction.
    b) ultrapurification of the lactic acid by ultrafiltration, nanofiltration and/or electrodialysis,
    c) concentration of the lactic acid and production of a prepolymer, d) cyclizing depolymerization to form the dilactide, e) purification of the dilactide, f) ring-opening polymerization of the dilactide, g) demonomerization of the polylactide.

2. Process according to claim 1, wherein in process step a) some of the external growth promoter components originally supplied with the nutrient solution and utilized by the bacteria is made available again to the activated cells directly in the fermentation circuit by lysis, which is realized thermally, by radiation or enzymes, of excess biomass formed.

3. Process according to claim 2, wherein the starch-containing agricultural products, are ground and a first part of the product is subjected to starch hydrolysis and the recovered glucose solution is reacted with a bacterium under anaerobic conditions in a fermenter, wherein the second part of the product is subjected to alkaline extraction and the protein extract obtained is supplied to the fermenter as a growth promoter source and the undissolved starch-containing residue is supplied to starch hydrolysis.

4. Process according to claim 3, wherein the starch-containing agricultural product is a grain.

5. Process according to claim 4, wherein the grain is selected from the group consisting of rye, wheat barley, triticale flour, maize, rice, and cassava.

6. Process according to claim 2 wherein the agricultural product is subjected to starch hydrolysis and the residual solid being produced during starch hydrolysis is additionally subjected to alkaline extraction and the protein extract obtained is supplied to the fermenter as growth promoter source.

7. Process according to claim 2, wherein the excess biomass obtained during fermentation is passed to a separate circuit, lysed there and then returned to the fermenter.

8. Process according to claim 2, wherein to maintain the concentration of the biomass in the fermenter at the required level via a regulating process, so much biomass is lysed per unit of time as biomass has grown.

9. Process according to claim 3, wherein starch hydrolysis, which is carried out in the form of a two-stage enzymatic process, is coupled with protein extract recovery.

10. Process according to claim 9, wherein the starch is liquefied in the first stage using the enzyme α-amylase and saccharified in the second stage using the enzyme glucoamylase.

11. Process according to claim 1, wherein the agricultural product is a grain.

12. Process according to claim 2, wherein individual or mixed cultures of the strains *Lactobacillus, Lactococcus, Streptococcus, Enterococcus* or *Pediococcus*, is used for fermentation.

13. Process according to claim 3, wherein the hydrolysate and/or the protein extract or the nutrient extract are sterilized.

14. Process according to claim 13, characterized in that the hydrolysate and the nutrient or protein extracts are sterilized separately.

15. Process according to claim 1, wherein fermentation is carried out continuously and the separation and purification of the lactic acid is effected using membrane separation processes.

16. Process according to claim 1, wherein the concentration (process step c)) is carried out so that an at least 90% strength lactic acid is present.

17. Process according to claim 16, wherein concentration is effected by two-stage evaporation and super-concentration, wherein the heat of condensation of the second stage is utilized for evaporation in the 1st stage.

18. Process according to claim 1, wherein the cyclizing depolymerization is carried out in a falling-film evaporator.

19. Process according to claim 1, wherein in process step e), purification is carried out to a hydroxyl group concentration <25 meq.

20. Process according to claim 18, wherein lactide purification takes place in a rectification column.

21. Process according to claim 1, wherein the ring-opening polymerization of the dilactide (process step f)) is carried out at a catalyst concentration of $2 \times 10^{-4}$ to $2 \times 10^{-5}$ mole per mole.

22. Process according to claim 1, wherein a stabilizer, which blocks the catalyst, is added before demonomerization.

23. Device for carrying out the process according to claim 1, comprising in each case at least one mixing device, a hydrolysis device, a fermenter, an ultrapurification device, a concentrator, a polycondensation device, a depolymerization device, an ultrapurification device for the dilactide, a reactor for polymerization and a demonomerization device.

24. Device according to claim 23, wherein the hydrolysis device is connected to at least one protein extractor.

25. Device according to claim 23, wherein the hydrolysis device has an ultrafiltration module situated in the external circuit.

26. Device according to claim 23, wherein at least one sterilisation device is connected upstream of the at least one fermenter.

27. Device according to claim 23, wherein the fermenter has an ultrafiltration module situated in the external circuit.

28. Device according to claim 23, wherein a nanofiltration device, a monopolar electrodialysis device and a bipolar electrodialysis device are provided connected in series as ultrapurification device.

29. Device according to claim 23, wherein the concentration device is designed to have three stages and consists of evaporators and arranged in series and a downstream superconcentrator.

30. Device according to claim 23, wherein the polycondensation device comprises two reactors and with an external circulating evaporator.

31. Device according to claim 23, wherein the depolymerization device is a falling-film evaporator.

32. Device according to claim 23, wherein the ultrapurification device for dilactide purification is at least one rectification column.

33. Device according to claim 23, wherein the reactor for ring-opening polymerization is a stirred vessel cascade having at least two reactors.

34. Device according claim 23, wherein the depolymerization device consists of a vacuum reactor and an annular disc reactor.

35. Device according to claim 23, wherein the depolymerization device has a thin-layer evaporator.

* * * * *